US012746033B2

(12) United States Patent
Fischer et al.

(10) Patent No.: US 12,746,033 B2
(45) Date of Patent: Sep. 29, 2026

(54) KNIFE HOUSING DESIGNS FOR ALIGNING A KNIFE WITH A KNIFE CAVITY

(71) Applicant: CILAG GMBH INTERNATIONAL, Zug (CH)

(72) Inventors: Austin Michael Fischer, Cincinnati, OH (US); Jeff Clark, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 60 days.

(21) Appl. No.: 18/984,710

(22) Filed: Dec. 17, 2024

(65) Prior Publication Data

US 2026/0165732 A1 Jun. 18, 2026

(51) Int. Cl.

| | |
|---|---|
| ***A61B 17/3211*** | (2006.01) |
| ***A61B 17/00*** | (2006.01) |
| ***A61B 17/28*** | (2006.01) |
| ***A61B 17/295*** | (2006.01) |
| *A61B 17/32* | (2006.01) |

(52) U.S. Cl.

CPC .... *A61B 17/3211* (2013.01); *A61B 17/00234* (2013.01); *A61B 17/28* (2013.01); *A61B 17/295* (2013.01); *A61B 2017/320074* (2017.08); *A61B 2017/320075* (2017.08); *A61B 2017/32113* (2013.01)

(58) Field of Classification Search

CPC .......... A61B 17/3211; A61B 17/00234; A61B 17/28; A61B 17/295; A61B 2017/320074; A61B 2017/320075; A61B 2017/32113

See application file for complete search history.

(56) References Cited

U.S. PATENT DOCUMENTS

| | | | | |
|---|---|---|---|---|
| 2015/0094720 | A1 | 4/2015 | Rooks et al. | |
| 2022/0226059 | A1 * | 7/2022 | Beckman | A61B 17/1285 |
| 2024/0090884 | A1 * | 3/2024 | Friedrich | A61B 90/11 |
| 2024/0293138 | A1 | 9/2024 | Dickerson et al. | |
| 2024/0299079 | A1 | 9/2024 | Fischer et al. | |

* cited by examiner

*Primary Examiner* — Michael J Carey

(74) *Attorney, Agent, or Firm* — Vorys, Sater, Seymour and Pease LLP

(57) ABSTRACT

A surgical tool includes a drive housing, a shaft extending distally from the drive housing, and an end effector arranged at an end of the shaft. The end effector includes a knife housing having opposing distal and proximal ends and opposing left and right walls extending from the distal end toward the proximal end, the left and right walls defining a knife cavity therebetween, a control surface defined on at least one of the left and right walls, and a knife having opposing distal and proximal ends and being moveable distally out of the knife cavity and proximally to a fully retracted position within the knife cavity. When the knife is moved proximally toward the fully retracted position, the proximal end of the knife is engageable with the control surface, which causes the knife to rotate into alignment with the knife cavity.

20 Claims, 10 Drawing Sheets

KNIFE HOUSING DESIGNS FOR ALIGNING A KNIFE WITH A KNIFE CAVITY

BACKGROUND

Minimally invasive surgical (MIS) instruments are often preferred over traditional open surgical devices due to reduced post-operative recovery time and minimal scarring. Laparoscopic surgery is one type of MIS procedure in which one or more small incisions are formed in the abdomen of a patient and a trocar is inserted through the incision to form a pathway that provides access to the abdominal cavity. Through the trocar, a variety of instruments and surgical tools can be introduced into the abdominal cavity. The instruments and tools introduced into the abdominal cavity via the trocar can be used to engage and/or treat tissue in a number of ways to achieve a diagnostic or therapeutic effect.

Various robotic systems have been developed to assist in MIS procedures. Robotic systems can allow for more instinctive hand movements by maintaining natural eye-hand axis. Robotic systems can also allow for more degrees of freedom in movement by including an articulable "wrist" joint that creates a more natural hand-like articulation. In such systems, an end effector positioned at the distal end of the instrument can be articulated (moved) using a cable driven motion system having one or more drive cables that extend through the wrist joint. A user (e.g., a surgeon) is able to remotely operate the end effector by grasping and manipulating in space one or more controllers that communicate with a tool driver coupled to the surgical instrument. User inputs are processed by a computer system incorporated into the robotic surgical system, and the tool driver responds by actuating the cable driven motion system. Moving the drive cables articulates the end effector to desired angular positions and configurations.

Some instruments include a cutting instrument or "knife" operable to traverse a jaw member through a guide track defined in the jaw member to sever tissue. The knife is often driven along the guide track by a drive rod extending through the wrist, and the drive rod is actuated to both push the knife distally and pull the knife back proximally, and pull the knife back to its home position.

At its home position, the knife is received within a knife housing, sometimes referred to as a "knife garage" or "distal wedge". To enter the knife housing, however, the knife must be oriented in a particular orientation that aligns with an opening to the knife housing, thereby allowing the knife to be properly received within the knife housing. If it is not properly oriented, the knife will be prevented from entering the knife housing and returning to its home position. What is needed is an improved system or assembly that helps properly orient the knife so that it can be successfully received within the knife housing upon being pulled proximally.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

FIG. 7 is an isometric view of a distal wedge according to a second embodiment with the surrounding elements removed.

DETAILED DESCRIPTION

The present disclosure is related to surgical tools and, more particularly, to a knife housing for a surgical tool end effector that includes a control surface designed to align a knife with a knife cavity as the knife is moved proximally toward the knife housing.

Embodiments disclosed herein describe a surgical tool that includes a drive housing, a shaft extending distally from the drive housing, and an end effector arranged at an end of the shaft. The end effector includes a knife housing having opposing distal and proximal ends and opposing left and right walls extending from the distal end toward the proximal end, the left and right walls defining a knife cavity therebetween, a control surface defined on at least one of the left and right walls, and a knife having opposing distal and proximal ends and being moveable distally out of the knife cavity and proximally to a fully retracted position within the knife cavity. When the knife is moved proximally toward the fully retracted position, the proximal end of the knife is engageable with the control surface, which causes the knife to rotate into alignment with the knife cavity.

In some embodiments, the control surface includes two control surfaces, one provided on each of the left and right walls, and wherein the proximal end of the knife slidably engages the control surfaces to align the knife with the knife cavity. In some embodiments, the control surfaces can each comprise a straight and angled surface, where the angled surface of one control surface is oppositely angled from the angled surface of the other control surface. In other embodiments, however, the control surfaces may each comprise a ramped and arcuate surface, where the arcuate surface of one control surface is inverse from the arcuate surface of the other control surface.

Figure 1:
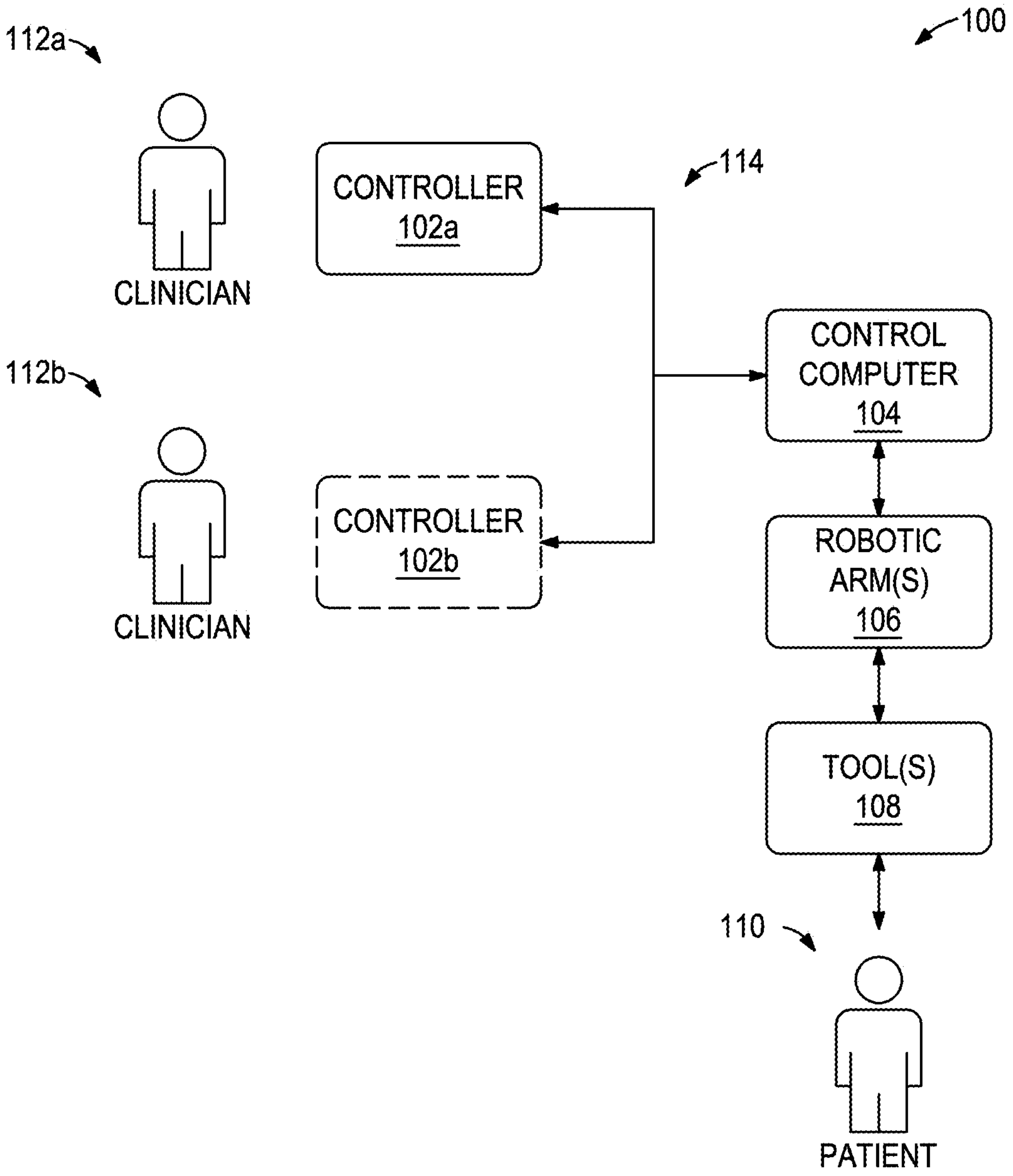
FIG. 1 is a block diagram of an example robotic surgical system that may incorporate some or all of the principles of the present disclosure.

FIG. 1 is a block diagram of an example robotic surgical system 100 that may incorporate some or all of the principles of the present disclosure. As illustrated, the system 100 can include at least one set of user input controllers 102*a* and at least one control computer 104. The control computer 104 may be mechanically and/or electrically coupled to a robotic manipulator and, more particularly, to one or more robotic arms 106 (alternately referred to as "tool drivers"). In some embodiments, the robotic manipulator may be included in or otherwise mounted to an arm cart capable of making the system portable. Each robotic arm 106 may include and otherwise provide a location for mounting one or more surgical instruments or tools 108 for performing various surgical tasks on a patient 110. Operation of the robotic arms 106 and associated tools 108 may be directed by a clinician 112*a* (e.g., a surgeon) from the user input controller 102*a*.

In some embodiments, a second set of user input controllers 102*b* (shown in dashed line) may be operated by a second clinician 112*b* to direct operation of the robotic arms 106 and tools 108 via the control computer 104 and in conjunction with the first clinician 112*a*. In such embodiments, for example, each clinician 112*a,b* may control different robotic arms 106 or, in some cases, complete control of the robotic arms 106 may be passed between the clinicians 112*a,b* as needed. In some embodiments, additional robotic manipulators having additional robotic arms may be utilized during surgery on the patient 110, and these additional robotic arms may be controlled by one or more of the user input controllers 102*a,b*.

The control computer 104 and the user input controllers 102*a,b* may be in communication with one another via a communications link 114, which may be any type of wired or wireless telecommunications means configured to carry a variety of communication signals (e.g., electrical, optical, infrared, etc.) according to any communications protocol. In some applications, for example, there is a tower with ancillary equipment and processing cores designed to drive the robotic arms 106.

The user input controllers 102*a,b* generally include one or more physical controllers that can be grasped by the clinicians 112*a,b* and manipulated in space while the surgeon views the procedure via a stereo display. The physical controllers generally comprise manual input devices movable in multiple degrees of freedom, and which often include an actuatable handle for actuating the surgical tool(s) 108, for example, for opening and closing opposing jaws, applying an electrical potential (current) to an electrode, or the like. The control computer 104 can also include an optional feedback meter viewable by the clinicians 112*a,b* via a display to provide a visual indication of various surgical instrument metrics, such as the amount of force being applied to the surgical instrument (i.e., a cutting instrument or dynamic clamping member).

Figures 2, 3:
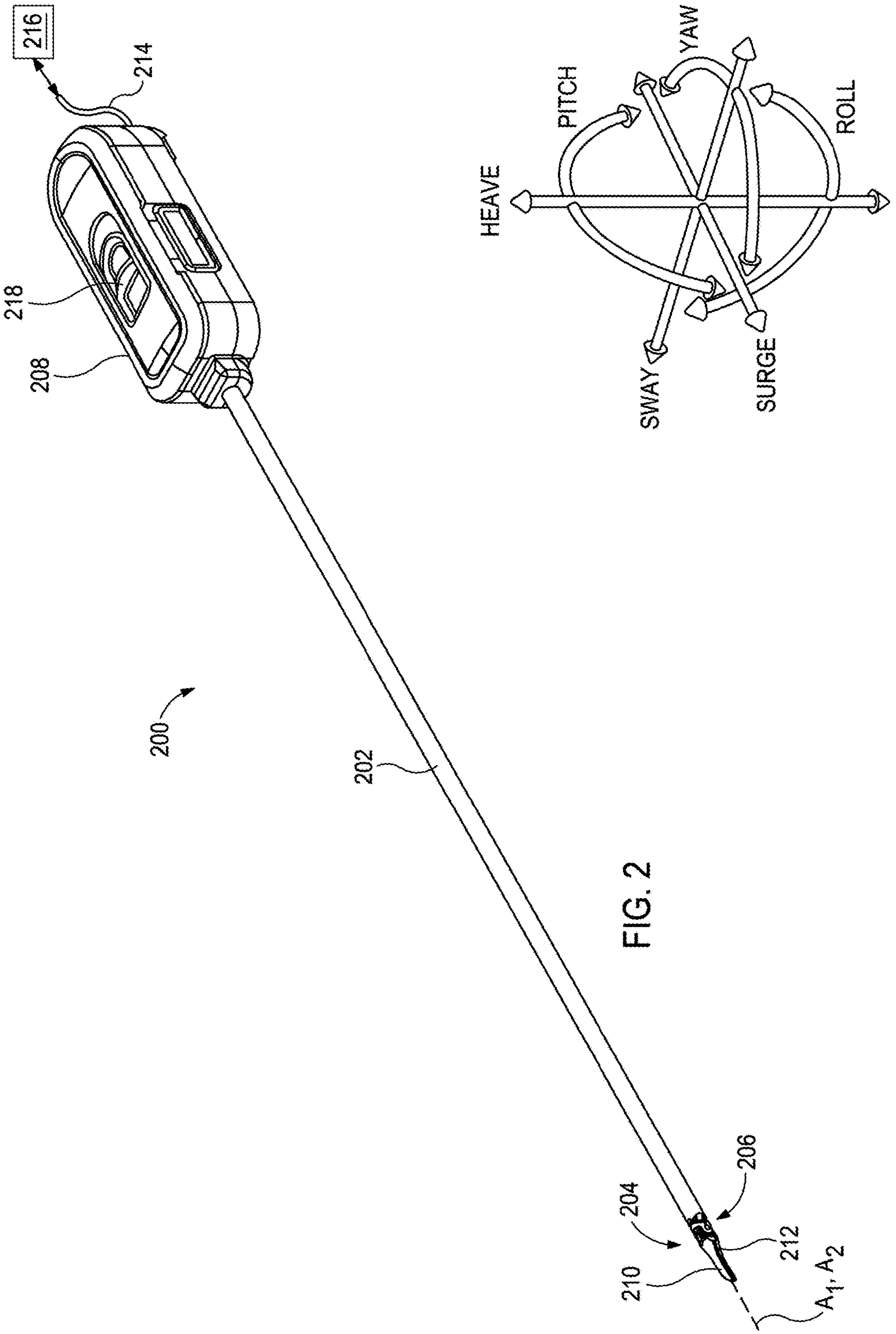
FIG. 2 is an isometric side view of an example surgical tool that may incorporate some or all of the principles of the present disclosure.
FIG. 3 illustrates potential degrees of freedom in which the wrist of the surgical tool of FIG. 2 may be able to articulate (pivot) and translate.

FIG. 2 is an isometric side view of an example surgical tool 200 that may incorporate some or all of the principles of the present disclosure. The surgical tool 200 may be the same as or similar to the surgical tool(s) 108 of FIG. 1 and, therefore, may be used in conjunction with a robotic surgical system, such as the robotic surgical system 100 of FIG. 1. Accordingly, the surgical tool 200 may be designed to be releasably coupled to a tool driver included in the robotic surgical system 100. In other embodiments, however, aspects of the surgical tool 200 may be adapted for use in a manual or hand-operated manner, without departing from the scope of the disclosure.

As illustrated, the surgical tool 200 includes an elongated shaft 202, an end effector 204, a wrist 206 (alternately referred to as a "wrist joint" or an "articulable wrist joint") that couples the end effector 204 to the distal end of the shaft 202, and a drive housing 208 coupled to the proximal end of the shaft 202. In applications where the surgical tool is used in conjunction with a robotic surgical system (e.g., the robotic surgical system 100 of FIG. 1), the drive housing 208 can include coupling features that releasably couple the surgical tool 200 to the robotic surgical system.

The terms "proximal" and "distal" are defined herein relative to a robotic surgical system having an interface configured to mechanically and electrically couple the surgical tool 200 (e.g., the housing 208) to a robotic manipulator. The term "proximal" refers to the position of an element closer to the robotic manipulator and the term "distal" refers to the position of an element closer to the end effector 204 and thus further away from the robotic manipulator. Alternatively, in manual or hand-operated applications, the terms "proximal" and "distal" are defined herein relative to a user, such as a surgeon or clinician. The term "proximal" refers to the position of an element closer to the user and the term "distal" refers to the position of an element closer to the end effector 204 and thus further away from the user. Moreover, the use of directional terms such as above, below, upper, lower, upward, downward, left, right, and the like are used in relation to the illustrative embodiments as they are depicted in the figures, the upward or upper direction being toward the top of the corresponding figure and the downward or lower direction being toward the bottom of the corresponding figure.

During use of the surgical tool 200, the end effector 204 is configured to move (pivot) relative to the shaft 202 at the wrist 206 to position the end effector 204 at desired orientations and locations relative to a surgical site. To accomplish this, the housing 208 includes (contains) various drive inputs and mechanisms (e.g., gears, actuators, etc.) designed to control operation of various features associated with the end effector 204 (e.g., clamping, firing, cutting, rotation, articulation, etc.). In at least some embodiments, the shaft 202, and hence the end effector 204 coupled thereto, is configured to rotate about a longitudinal axis $A_1$ of the shaft 202. In such embodiments, at least one of the drive inputs included in the housing 208 is configured to control rotational movement of the shaft 202 about the longitudinal axis $A_1$.

The shaft 202 is an elongate member extending distally from the housing 208 and has at least one lumen extending therethrough along its axial length. In some embodiments, the shaft 202 may be fixed to the housing 208, but could alternatively be rotatably mounted to the housing 208 to allow the shaft 202 to rotate about the longitudinal axis $A_1$. In yet other embodiments, the shaft 202 may be releasably coupled to the housing 208, which may allow a single housing 208 to be adaptable to various shafts having different end effectors.

The end effector 204 can exhibit a variety of sizes, shapes, and configurations. In the illustrated embodiment, the end effector 204 comprises a combination tissue grasper and vessel sealer that include opposing first (upper) and second (lower) jaws 210, 212 configured to move (articulate) between open and closed positions. As will be appreciated, however, the opposing jaws 210, 212 may alternatively form part of other types of end effectors such as, but not limited to, a surgical scissors, a clip applier, a needle driver, a babcock including a pair of opposed grasping jaws, bipolar jaws (e.g., bipolar Maryland grasper, forceps, a fenestrated grasper, etc.), etc. One or both of the jaws 210, 212 may be configured to pivot to articulate the end effector 204 between the open and closed positions.

FIG. 3 illustrates the potential degrees of freedom in which the wrist 206 may be able to articulate (pivot) and thereby move the end effector 204. The wrist 206 can have any of a variety of configurations. In general, the wrist 206 comprises a joint configured to allow pivoting movement of the end effector 204 relative to the shaft 202. The degrees of freedom of the wrist 206 are represented by three translational variables (i.e., surge, heave, and sway), and by three rotational variables (i.e., Euler angles or roll, pitch, and yaw). The translational and rotational variables describe the position and orientation of the end effector 204 with respect to a given reference Cartesian frame. As depicted in FIG. 3, "surge" refers to forward and backward translational movement, "heave" refers to translational movement up and down, and "sway" refers to translational movement left and right. With regard to the rotational terms, "roll" refers to tilting side to side, "pitch" refers to tilting forward and backward, and "yaw" refers to turning left and right.

The pivoting motion can include pitch movement about a first axis of the wrist 206 (e.g., X-axis), yaw movement about a second axis of the wrist 206 (e.g., Y-axis), and combinations thereof to allow for 360° rotational movement of the end effector 204 about the wrist 206. In other applications, the pivoting motion can be limited to movement in a single plane, e.g., only pitch movement about the first axis of the wrist 206 or only yaw movement about the second axis of the wrist 206, such that the end effector 204 moves only in a single plane.

Referring again to FIG. 2, the surgical tool 200 may also include a plurality of drive cables (obscured in FIG. 2) that form part of a cable driven motion system configured to facilitate actuation and articulation of the end effector 204 relative to the shaft 202. Moving (actuating) one or more of the drive cables moves the end effector 204 between an unarticulated position and an articulated position. The end effector 204 is depicted in FIG. 2 in the unarticulated position where a longitudinal axis $A_2$ of the end effector 204 is substantially aligned with the longitudinal axis $A_1$ of the shaft 202, such that the end effector 204 is at a substantially zero angle relative to the shaft 202. Due to factors such as manufacturing tolerance and precision of measurement devices, the end effector 204 may not be at a precise zero angle relative to the shaft 202 in the unarticulated position, but nevertheless be considered "substantially aligned" thereto. In the articulated position, the longitudinal axes $A_1$, $A_2$ would be angularly offset from each other such that the end effector 204 is at a non-zero angle relative to the shaft 202.

In some embodiments, the surgical tool 200 may be supplied with electrical power (current) via a power cable 214 coupled to the housing 208. In other embodiments, the power cable 214 may be omitted and electrical power may be supplied to the surgical tool 200 via an internal power source, such as one or more batteries, capacitors, or fuel cells. In such embodiments, the surgical tool 200 may alternatively be characterized and otherwise referred to as an "electrosurgical instrument" capable of providing electrical energy to the end effector 204.

The power cable 214 may place the surgical tool 200 in electrical communication with a generator 216 that supplies energy, such as electrical energy (e.g., radio frequency energy), ultrasonic energy, microwave energy, heat energy, or any combination thereof, to the surgical tool 200 and, more particularly, to the end effector 204. Accordingly, the generator 216 may comprise a radio frequency (RF) source, an ultrasonic source, a direct current source, and/or any other suitable type of electrical energy source that may be activated independently or simultaneously.

In applications where the surgical tool 200 is configured for bipolar operation, the power cable 214 will include a supply conductor and a return conductor. Current can be supplied from the generator 216 to an active (or source) electrode located at the end effector 204 via the supply conductor, and current can flow back to the generator 216 via a return electrode located at the end effector 204 via the return conductor. In the case of a bipolar grasper with opposing jaws, for example, the jaws serve as the electrodes where the proximal end of the jaws are isolated from one another and the inner surface of the jaws (i.e., the area of the jaws that grasp tissue) apply the current in a controlled path through the tissue. In applications where the surgical tool 200 is configured for monopolar operation, the generator 216 transmits current through a supply conductor to an active electrode located at the end effector 204, and current is returned (dissipated) through a return electrode (e.g., a grounding pad) separately coupled to a patient's body.

The surgical tool 200 may further include a manual release switch 218 that may be manually actuated by a user (e.g., a surgeon) to override the cable driven system and thereby manually articulate or operate the end effector 204. The release switch 218 is movably positioned on the drive housing 208, and a user is able to manually move (slide) the release switch 218 from a disengaged position, as shown, to an engaged position. In the disengaged position, the surgical tool 200 is able to operate as normal. As the release switch 218 moves to the engaged position, however, various internal component parts of the drive housing 208 are simultaneously moved, thereby resulting in the jaws 210, 212 opening, which might prove beneficial for a variety of reasons. In some applications, for example, the release switch 218 may be moved in the event of an electrical disruption that renders the surgical tool 200 inoperable. In such applications, the user would be able to manually open the jaws 210, 212 and thereby release any grasped tissue and remove the surgical tool 200. In other applications, the release switch 218 may be actuated (enabled) to open the jaws 210, 212 in preparation for cleaning and/or sterilization of the surgical tool 200.

Figure 4A:
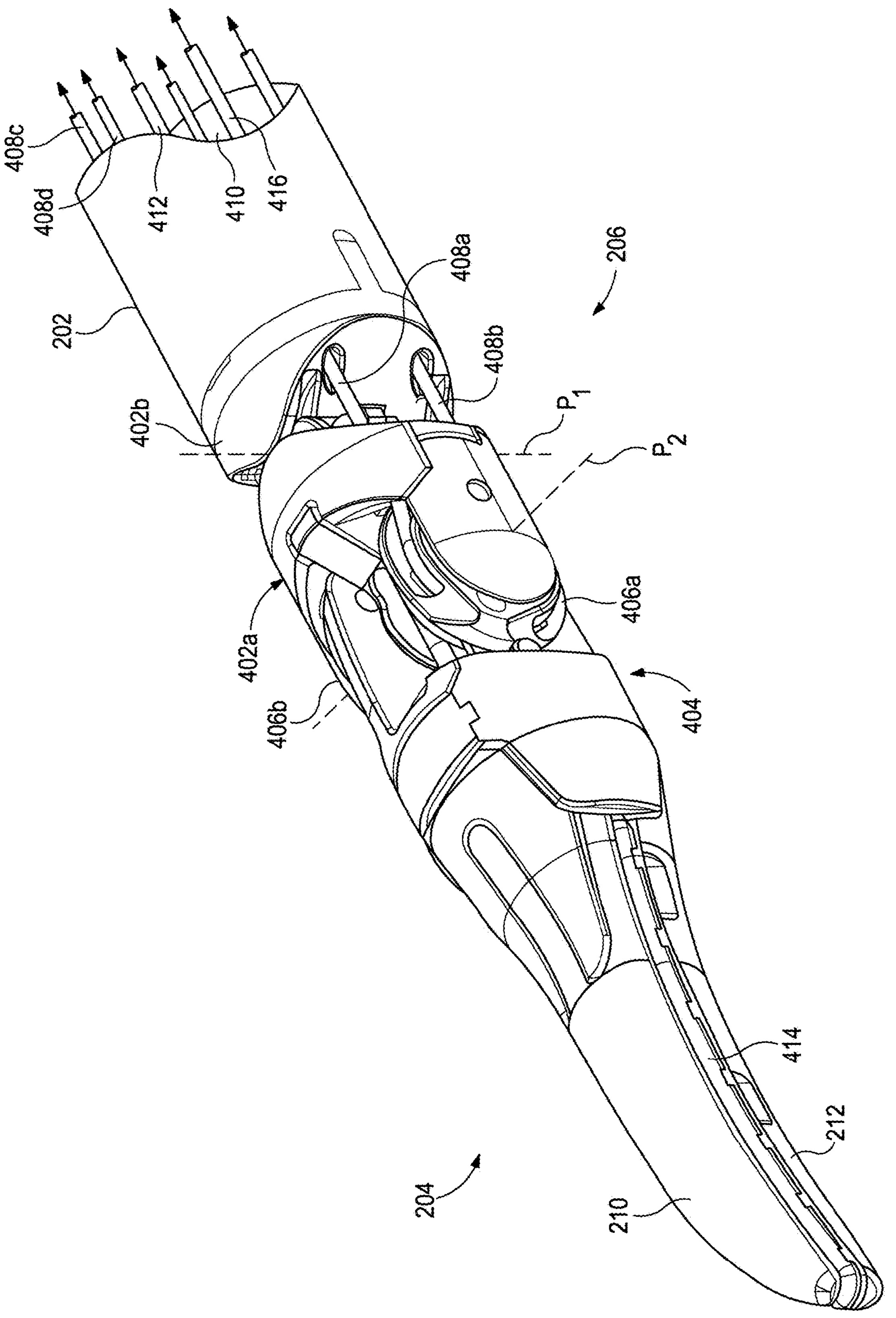
FIG. 4A is an enlarged isometric view of the distal end of the surgical tool of FIG. 2.

FIG. 4A is an enlarged isometric view of the distal end of the surgical tool 200. More specifically, FIG. 4A depicts an enlarged view of the end effector 204 and the wrist 206, with the jaws 210, 212 of the end effector 204 in the closed position. The wrist 206 operatively couples the end effector 204 to the shaft 202. In some embodiments, however, a shaft adapter may be directly coupled to the wrist 206 and otherwise interpose the shaft 202 and the wrist 206. Accordingly, the wrist 206 may be operatively coupled to the shaft 202 either through a direct coupling engagement where the wrist 206 is directly coupled to the distal end of the shaft 202, or an indirect coupling engagement where a shaft adapter interposes the wrist 206 and the distal end of the shaft 202. As used herein, the term "operatively couple" refers to a direct or indirect coupling engagement between two components.

To operatively couple the end effector 204 to the shaft 202, the wrist 206 includes a first or "distal" clevis 402_a_ and a second or "proximal" clevis 402_b_. The clevises 402_a,b_ are alternatively referred to as "articulation joints" of the wrist 206 and extend from the shaft 202 (or alternatively a shaft adapter). The clevises 402*a,b* are operatively coupled to facilitate articulation of the wrist 206 relative to the shaft 202. As illustrated, the wrist 206 also includes a linkage 404 arranged distal to the distal clevis 402*a* and operatively mounted to the jaws 210, 212.

The proximal end of the distal clevis 402*a* may be rotatably mounted or pivotably coupled to the proximal clevis 402*b* at a first pivot axis $P_1$ of the wrist 206. In some embodiments, an axle may extend through the first pivot axis $P_1$ and the distal and proximal clevises 402*a,b* may be rotatably coupled via the axle. In other embodiments, however, such as is depicted in FIG. 4A, the distal and proximal clevises 402*a,b* may be engaged in rolling contact, such as via an intermeshed gear relationship that allows the clevises 402*a,b* to rotate relative to each other similar to a rolling joint.

First and second pulleys 406*a* and 406*b* may be rotatably mounted to the distal end of the distal clevis 402*a* at a second pivot axis $P_2$ of the wrist 206. The linkage 404 may be arranged distal to the second pivot axis $P_2$ and operatively mounted to the jaws 210, 212. The first pivot axis $P_1$ is substantially perpendicular (orthogonal) to the longitudinal axis $A_1$ of the shaft 202, and the second pivot axis $P_2$ is substantially perpendicular (orthogonal) to both the longitudinal axis $A_1$ and the first pivot axis $P_1$. Movement of the end effector 204 about the first pivot axis $P_1$ provides "yaw" articulation of the wrist 206, and movement about the second pivot axis $P_2$ provides "pitch" articulation of the wrist 206.

A plurality of drive cables, shown as drive cables 408*a*, 408*b*, 408*c*, and 408*d*, extend longitudinally within a lumen 410 defined by the shaft 202 (or a shaft adaptor) and extend at least partially through the wrist 206. The drive cables 408*a-d* may form part of the cable driven motion system housed within the drive housing 208 (FIG. 2), and may comprise cables, bands, lines, cords, wires, woven wires, ropes, strings, twisted strings, elongate members, belts, shafts, flexible shafts, drive rods, or any combination thereof. The drive cables 408*a-d* can be made from a variety of materials including, but not limited to, a metal (e.g., tungsten, stainless steel, nitinol, etc.), a polymer (e.g., ultra-high molecular weight polyethylene), a synthetic fiber (e.g., KEVLAR®, VECTRAN®, etc.), an elastomer, or any combination thereof. While four drive cables 408*a-d* are depicted in FIG. 4A, more or less than four may be employed, without departing from the scope of the disclosure.

The drive cables 408*a-d* extend proximally from the end effector 204 and the wrist 206 toward the drive housing 208 (FIG. 2) where they are operatively coupled to various actuation mechanisms or devices that facilitate longitudinal movement (translation) of the drive cables 408*a-d* within the lumen 410. Selective actuation of the drive cables 408*a-d* applies tension (i.e., pull force) to the given drive cable 408*a-d* in the proximal direction, which urges the given drive cable 408*a-d* to translate longitudinally within the lumen 410.

In the illustrated embodiment, the drive cables 408*a-d* each extend longitudinally through the proximal clevis 402*b*. The distal end of each drive cable 408*a-d* terminates at the first or second pulleys 406*a,b*, thus operatively coupling each drive cable 408*a-d* to the end effector 204. In some embodiments, the distal ends of the first and second drive cables 408*a,b* may be coupled to each other and terminate at the first pulley 406*a*, and the distal ends of the third and fourth drive cables 408*c*, d may be coupled to each other and terminate at the second pulley 406*b*. In at least one embodiment, the distal ends of the first and second drive cables 408*a,b* and the distal ends of the third and fourth drive cables 408*c*, d may each be coupled together at corresponding ball crimps (not shown) mounted to the first and second pulleys 406*a,b*, respectively.

In at least one embodiment, the drive cables 408*a-d* may operate "antagonistically". More specifically, when the first drive cable 408*a* is actuated (moved), the second drive cable 408*b* naturally follows as coupled to the first drive cable 408*a*, and when the third drive cable 408*c* is actuated, the fourth drive cable 408*d* naturally follows as coupled to the third drive cable 408*c*, and vice versa. Antagonistic operation of the drive cables 408*a-d* can open or close the jaws 210, 212. More specifically, selective actuation of the drive cables 408*a-d* in other known configurations or coordination will cause the jaws 210, 212 to open or close. Antagonistic operation of the drive cables 408*a-d* can further cause the end effector 204 to articulate at the wrist 206. More specifically, selective actuation of the drive cables 408*a-d* in known configurations or coordination can cause the end effector 204 to articulate about one or both of the pivot axes $P_1$, $P_2$, thus facilitating articulation of the end effector 204 in both pitch and yaw directions, either individually or simultaneously. Antagonistic operation of the drive cables 408*a-d* advantageously reduces the number of cables required to provide full wrist 206 motion, and also helps eliminate slack in the drive cables 408*a-d*, which results in more precise motion of the end effector 204.

In the illustrated embodiment, the end effector 204 is able to articulate (move) in pitch about the second or "pitch" pivot axis $P_2$, which is located near the distal end of the wrist 206. Thus, the jaws 210, 212 open and close in the direction of pitch. In other embodiments, however, the wrist 206 may alternatively be configured such that the second pivot axis $P_2$ facilitates yaw articulation of the jaws 210, 212, without departing from the scope of the disclosure.

In some embodiments, an electrical conductor 412 may also extend longitudinally within the lumen 410, through the wrist 206, and terminate at an electrode 414 to supply electrical energy to the end effector 204. In some embodiments, the electrical conductor 412 may comprise a wire, but may alternatively comprise a rigid or semi-rigid shaft, rod, or strip (ribbon) made of a conductive material. The electrical conductor 412 may be entirely or partially covered with an insulative covering (overmold) made of a non-conductive material. Using the electrical conductor 412 and the electrode 414, the end effector 204 may be configured for monopolar or bipolar RF operation.

In the illustrated embodiment, the end effector 204 comprises a combination tissue grasper and vessel sealer that includes a knife 420 (FIG. 4B), alternately referred to as a "cutting element" or "blade member." The knife 420 is aligned with and configured to traverse a guide track 422 (FIG. 4B) defined longitudinally in one or both of the upper and lower jaws 210, 212. The knife 420 may be operatively coupled to the distal end of a drive rod 416 that extends longitudinally within lumen 410 and passes through the wrist 206. Longitudinal movement (translation) of the drive rod 416 correspondingly moves the knife 420 within the guide track(s) 422. Similar to the drive cables 408*a-d*, the drive rod 416 may form part of the actuation systems housed within the drive housing 208 (FIG. 2). Selective actuation of a corresponding drive input will cause the drive rod 416 to move distally or proximally within the lumen 410, and correspondingly move the knife 420 in the same longitudinal direction.

Figure 4B:
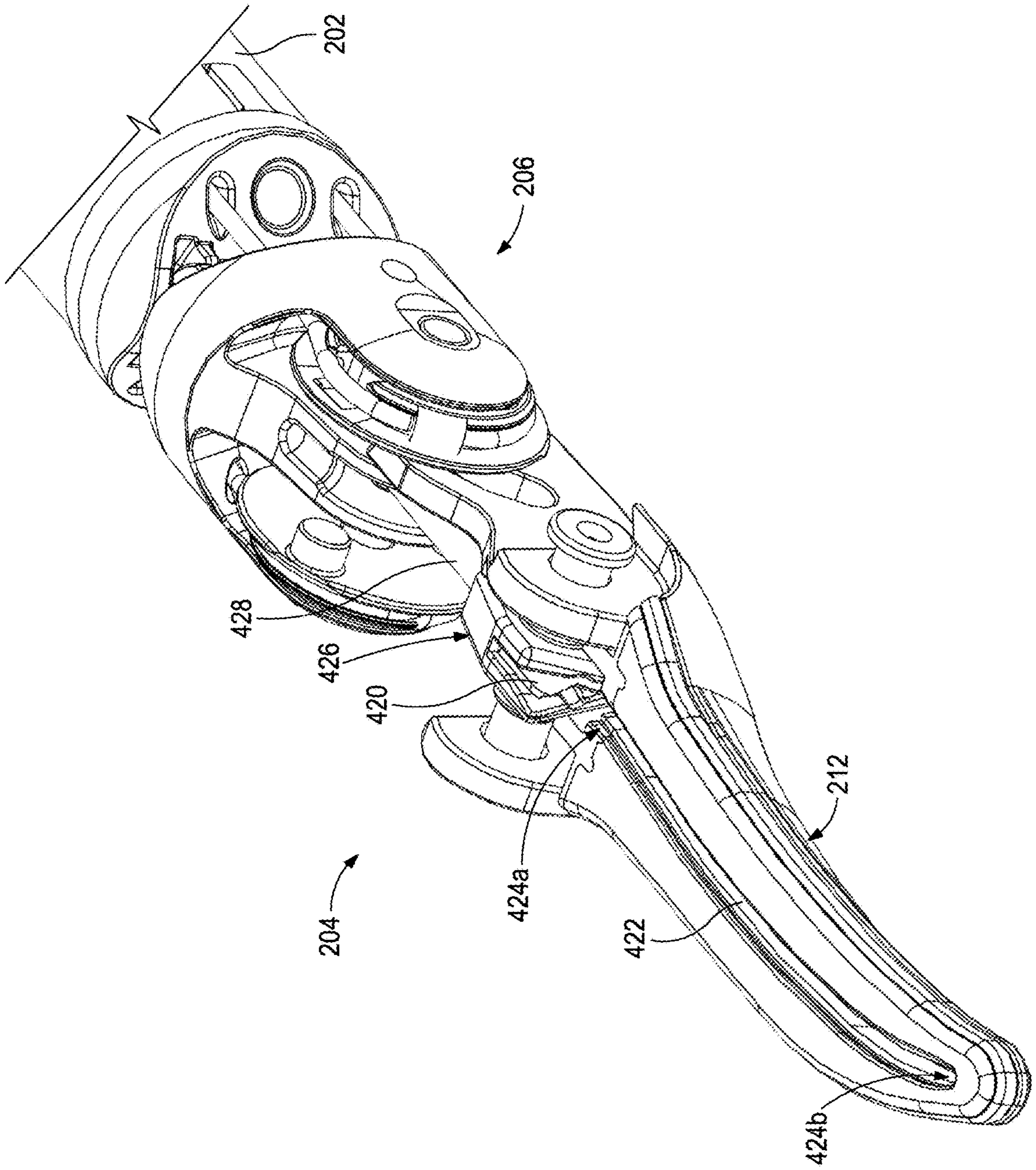
FIG. 4B is a partial isometric view of the distal end of the surgical tool of FIG. 2 with a jaw removed.

FIG. 4B is a partial isometric view of the end effector 204 with the first jaw 210 (FIG. 4A) removed. As illustrated, at least a portion of the guide track 422 is defined in the second jaw 212 and extends from a proximal end 424*a* to a distal end 424*b*. In some embodiments, however, the first jaw 210 may include a similar or complimentary guide track opposite the guide track 422 shown in FIG. 4B when the first and second jaws 210, 212 are closed. The knife 420 (partially visible) is illustrated as being received or otherwise disposed within a knife housing 426 (alternately referred to as a "distal wedge") arranged adjacent the proximal end 424*a* of the guide track 422. When the knife 420 is properly and fully received within the knife housing 426, the knife 420 may be characterized as being in a "zero" or "home" position. When the knife 420 exits the knife housing 426 and enters the guide track 422, the knife 420 may be characterized as being in a "deployed" position.

The knife housing 426 may be constructed of a non-conductive material and as a separate component. When the knife 420 is in the home position within the knife housing 426, the end effector 204 may be safely handled for cleaning or maintenance. Moreover, returning the knife 420 to the home position during normal operation will help ensure the knife 420 is not exposed during grasping and manipulation of tissue.

In operation, the knife 420 may be selectively moved distally out of the knife housing 426 along the guide track 422 by longitudinally moving the drive rod 416 as described above.

In some embodiments, as illustrated, a rod sheath 428 is operatively coupled to the knife housing 426 and otherwise extends proximally from the knife housing 426 and through the wrist 206. The rod sheath 428 may comprise a flexible tubular or lumen sized to receive the drive rod 416 (FIG. 4A), which is operatively coupled to the knife 420. The drive rod 416 may be configured to translate within the rod sheath 428 during example operation, and thereby advance or retract the knife 420 along the guide track 422. Since they extend through the wrist 206, the drive rod 416 and the rod sheath 428 may be constructed of a flexible material to allow the wrist 206 to articulate the end effector 204 with respect to the shaft 202. Example flexible materials include, but are not limited to, a metal (e.g., titanium, tungsten, nitinol, stainless-steel, etc.), a polymer (e.g., ultra-high molecular weight polyethylene), a composite material (e.g., carbon fiber), or any combination thereof.

In some embodiments, the end effector may comprise an advanced bipolar device, and the jaws 210 (FIGS. 2 and 4A), 212 may pivot simultaneously between the open and closed positions, which may be advantageous in creating symmetry across the jaws 210, 212. In such embodiments, however, a centerline of the knife 420 travels between the two jaws 210, 212, and because the knife 420 is not captured within either of the jaws 210, 212, the knife 420 can potentially become exposed if the jaw aperture is too large when the knife 420 is deployed. This can result in the knife 420 rotating relative to the knife housing 426 and, therefore, not being able to fully return to the home position within the knife housing 426.

According to embodiments of the present disclosure, and as described in greater detail below, the knife housing 426 may provide and otherwise define one or more camming or "control" surfaces operable to reorient the knife 420 so that it can be properly received within the knife housing 426. As the drive rod 416 (FIG. 4A) pulls the knife 420 proximally, the proximal end of the knife 420 will eventually contact the control surface(s), and the reaction forces provided by the control surfaces will cause knife 420 to rotate until the knife 420 is substantially aligned with the opening to the knife housing 426, thereby allowing the knife 420 to fully retract into its home position.

Figure 5A:
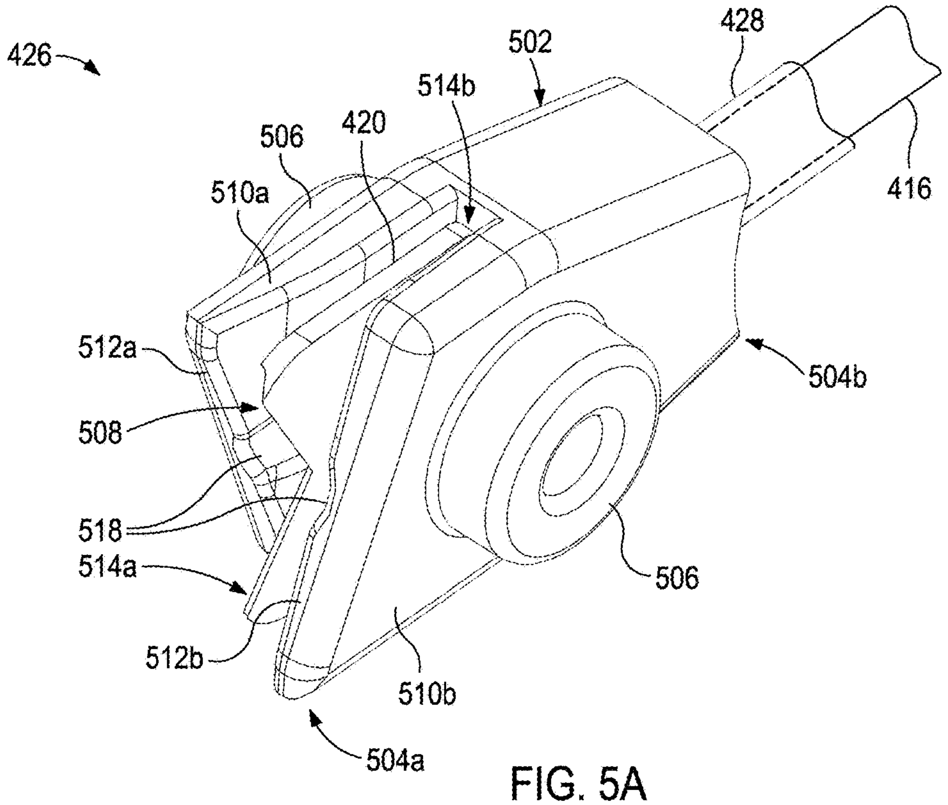
FIGS. 5A and 5B are isometric and side views, respectively, of the knife housing of FIG. 4B, according to one or more embodiments of the present disclosure.
Figure 5B:
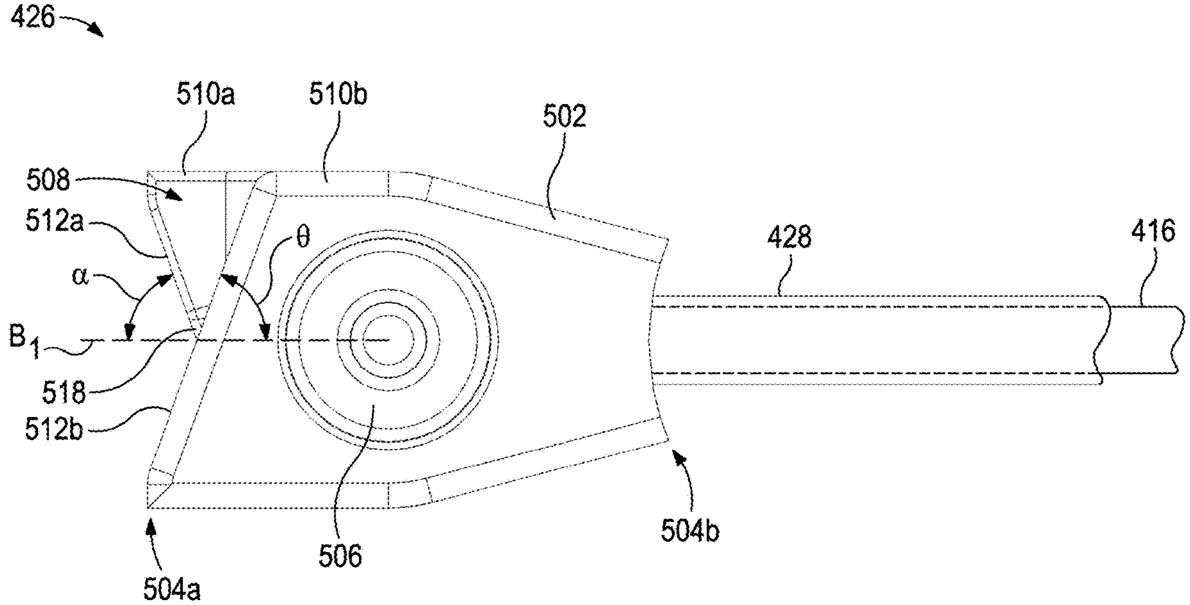

FIGS. 5A and 5B are isometric and side views, respectively, of an example of the knife housing 426, according to one or more embodiments of the present disclosure. As illustrated, the knife housing 426 includes a housing body 502 including a first or "distal" end 504*a* and a second or "proximal" end 504*b* opposite the distal end 504*a*. The rod sheath 428 may extend from the proximal end 504*b*. In some embodiments, the knife housing 426 and the rod sheath 428 may be integrally formed as a monolithic part. In other embodiments, however, the rod sheath 428 may comprise a separate component part from the knife housing 426. In such embodiments, the rod sheath may be operatively coupled to the knife housing 426.

The drive rod 416 is operatively coupled to the knife 420 (FIG. 5A) such that longitudinal movement of the drive rod 416 correspondingly moves the knife 420 relative to the knife housing 426. As illustrated, the drive rod 416 extends within the rod sheath 428 and is able to longitudinally translate within the rod sheath 428 during operation.

In some embodiments, as illustrated, a boss 506 is provided and otherwise defined on each lateral side of the housing body 502. The boss(es) 506 may be rotatably mounted to portions of the jaws 210, 212 (FIGS. 2 and 4A), and thereby help the knife housing 426 rotate as the wrist 216 (FIGS. 2 and 4A-4B) articulates.

The knife housing 426 may further define a knife cavity or "garage" 508 sized to receive the knife 420. When the knife 420 is fully received within the knife cavity 508, the knife 420 may be characterized as being in a "fully retracted" or "home" position. Upon firing the end effector 204 (FIGS. 2 and 4A-4B), the drive rod 416 is moved (urged) distally, which correspondingly moves the knife 420 out of the knife cavity 508 and into the guide track 422 (FIG. 4A). After firing is complete, the drive rod 416 is retracted proximally, which pulls the knife 420 proximally and back into the knife cavity 508 until it is desired to fire the end effector 204 again.

In the illustrated embodiment, the knife cavity 508 is defined by the housing body 502, which provides opposing first (left) and second (right) walls 510*a* and 510*b* that extend from the distal end 504*a* of the knife housing 426 and toward the proximal end 504*b*. The knife cavity 508 encompasses a gap defined between the first and second walls 510*a,b*. In the illustrated embodiment, the walls 510*a,b* extend substantially parallel to each other and terminate in corresponding control surfaces 512*a* and 512*b* configured to engage and reorient the knife 420 into proper alignment with the knife cavity 508. In the illustrated embodiment, each wall 510*a,b* provides a corresponding control surface 512*a,b*. In other embodiments, however, only one control surface 512*a,b* may be required to properly reorient the knife 420 into alignment with the knife cavity 508.

In the illustrated embodiment, the control surfaces 512*a,b* each comprise straight and angled surfaces, where the control surfaces 512*a,b* are oppositely angled. More specifically, and as best seen in FIG. 5B, the second control surface 512*b* may extend at an angle θ from a centerline $B_1$ of the knife housing 426, and the first control surface 512*a* may extend at an angle α from the centerline $B_1$, where the angle θ comprises a positive angle magnitude, measured counter-clockwise from centerline $B_1$, and the angle α comprises a negative angle magnitude, measured clockwise from centerline $B_1$. The angle θ may range between about 5° and about 85°, and the angle α may range between about −5° and about −85°. In some embodiments, the angles θ, α may be the same but opposite (e.g., angle θ=45° and angle α=−45°). In other embodiments, the angles θ, α may have different magnitudes, but opposite each other over a line perpendicular to centerline $B_1$, (e.g., angle θ=35° and angle α=−55°), without departing from the scope of the disclosure. Accordingly, as used herein, the term "oppositely angled" can refer to angles that have the same or different magnitudes but in positive and negative directions relative to the centerline $B_1$.

As best seen in FIG. 5A, the knife 420 has a first or "distal" end 514*a* and a second or "proximal" end 514*b* opposite the distal end 514*a*. In some embodiments, the knife 420 may be fabricated of stainless-steel (e.g., 420 or 440 stainless steel) or other metallic materials. A cutting edge 516 is provided and otherwise formed at the distal end 514*a* of the knife 420. In some embodiments, as illustrated, the cutting edge 516 may be V-shaped, but could alternatively be straight or exhibit any other geometry suitable to achieve desirable cutting properties. The knife 420 may be distally extended through the guide track 422 (FIG. 4B) to sever tissue with the cutting edge 516.

The drive rod 416 may be operatively coupled to the proximal end 514*b* of the knife 420. In some embodiments, the drive rod 416 may be operatively coupled to the knife 420 using a ferrule (not shown). In such embodiments, one or more grooves 518 may be defined within the knife cavity 508 (e.g., on the inner surfaces of the walls 510*a,b*) to accommodate the shape of the ferrule. Moreover, in such embodiments, the grooves 518 may extend parallel to the centerline $B_1$.

Figure 6:
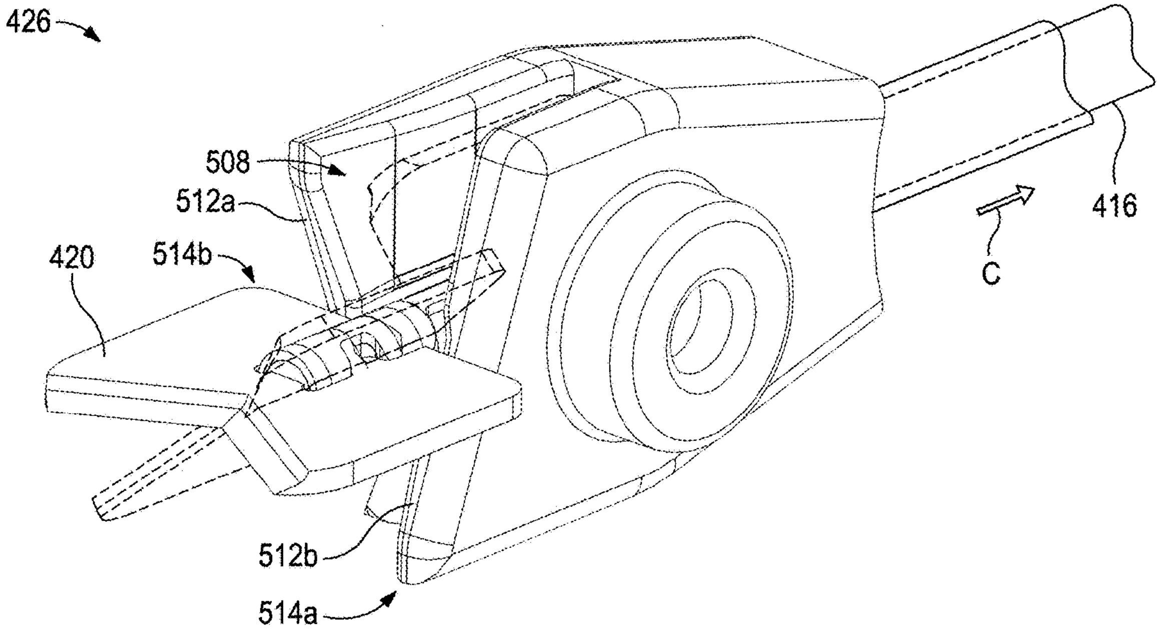
FIG. 6 is an isometric view of knife housing of FIGS. 5A-5B showing example operation of reorienting the knife, according to one or more embodiments.

FIG. 6 is an isometric view of the knife housing 426 showing example operation of reorienting the knife 420, according to one or more embodiments. As the drive rod 416 is moved proximally, as shown by the arrow C, the proximal end 514*b* of the knife 420 will eventually locate and engage the distal end 504*a* of the knife housing 426 and, more particularly, the control surfaces 512*a,b*. If the knife 410 is not oriented properly to be received within the knife cavity 508, engaging the oppositely angled control surfaces 512*a,b* as the knife 420 moves proximally C will cause the knife 420 to rotate until aligning with the knife cavity 508.

In the illustrated example, the knife 420 is shown oriented generally horizontal as it approaches the knife housing 426 in the direction C. In this orientation, the knife 420 will be unable to enter knife cavity 508, which is oriented generally vertical. Upon reaching the knife housing 426, the proximal end 514*b* of the knife 420 engages the control surfaces 512*a,b*, which causes the knife 420 to rotate into alignment with the knife cavity 508 as the knife 420 continues in the proximal direction C. Because the control surfaces 512*a,b* are oppositely angled, the knife 420 is induced into rotation to align with the knife cavity 508. Once aligned with the knife cavity 508, further movement of the drive rod 416 in the proximal direction C will correspondingly cause the knife 420 to enter the knife cavity 508 and ultimately reach its home position.

Figure 7:
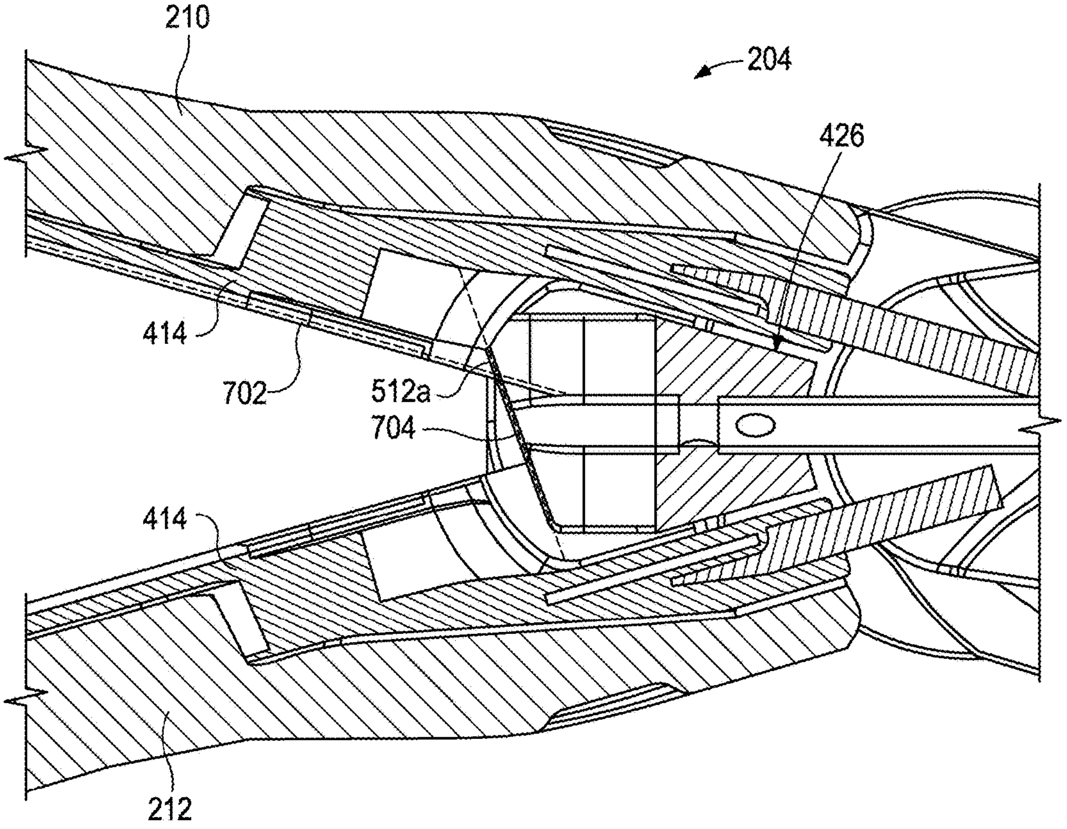
FIG. 7 is an enlarged cross-sectional side view of the end effector and the knife housing, according to one or more embodiments.

FIG. 7 is an enlarged cross-sectional side view of a portion of the end effector 204 and the knife housing 426, according to one or more embodiments of the present disclosure. The knife 420 and the drive rod 416 are omitted to enable viewing of the geometry of the knife housing 426, and the jaws 210, 212 are in the fully open position. In the illustrated embodiment, both jaws 210, 212 include corresponding and opposing electrodes 414 that form the bottom and top surfaces, respectively, of the jaws 210, 212.

When the jaws 210, 212 are in the fully open position, a plane 702 extending along and passing through the exposed surface of the upper electrode 414 will intersect the control surface 512*a* of the knife housing 426, as indicated by the dashed line 704. This ensures that the knife 420 (FIGS. 5A-5B and 6) will always engage the control surface 512*a* upon being moved proximally C (FIG. 6) rather than inadvertently traversing (accessing) above or below the knife housing 426 and potentially jamming the knife 420 out of plane with the knife housing 426. The control surface 512*a* may also have a length sufficient to prevent the knife 426 from traversing above the knife housing 426 when the jaws 210, 212 are fully opened. More specifically, when the jaws 210, 212 are fully opened, the control surface 512*a* penetrates the plane 702 extending along the upper electrode 414.

Figure 8:
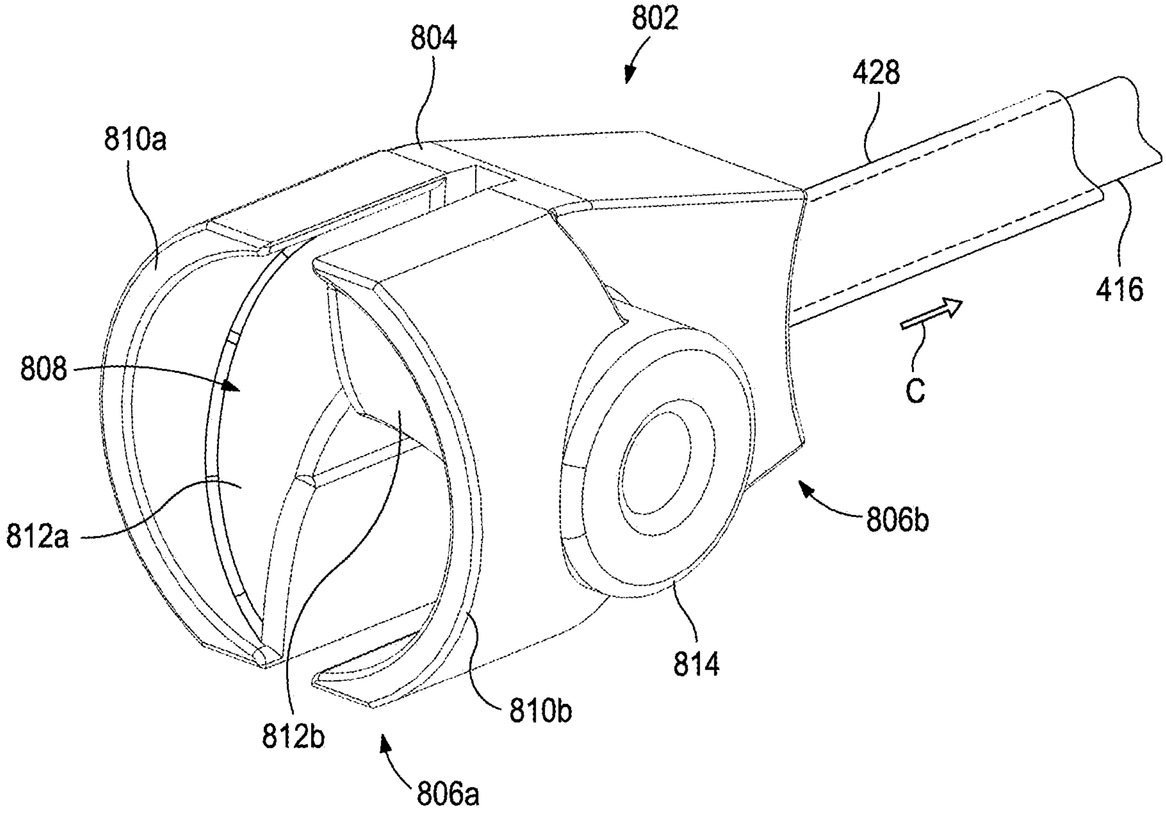
FIG. 8 is an isometric view of another embodiment of the knife housing, according to one or more additional embodiments.

FIG. 8 is an isometric view of another example knife housing 802, according to one or more additional embodiments of the present disclosure. The knife housing 802 may be similar in some respects to the knife housing 426 of FIGS. 5A-5B, and therefore may be best understood with reference thereto. Similar to the knife housing 426, for example, the knife housing 802 may be used in conjunction with the knife 420 (FIGS. 4B, 5A, and 6) and the drive rod 416. The knife 420 is omitted from FIG. 8 to enable discussion of the structural features of the knife housing 802.

As illustrated, the knife housing 802 includes a housing body 804 including a first or "distal" end 806*a* and a second or "proximal" end 806*b* opposite the distal end 806*a*. The rod sheath 428 extends from the proximal end 806*b*, and may either be integrally formed with the knife housing 802 as a monolithic part or may alternatively comprise a separate component part operatively coupled to the knife housing 802. The drive rod 416 is operatively coupled to the knife 420 (FIGS. 4B, 5A, and 6) such that longitudinal movement of the drive rod 416 correspondingly moves the knife 420 relative to the knife housing 802.

In some embodiments, as illustrated, a boss 814 may be provided and otherwise defined on each lateral side of the housing body 804. The boss(es) 814 may be rotatably mounted to portions of the jaws 210, 212 (FIGS. 2 and 4A), and may help the knife housing 802 rotate as the wrist 216 (FIGS. 2 and 4A-4B) articulates.

The knife housing 802 may further define a knife cavity or "garage" 808 sized to receive the knife 420 (FIGS. 4B, 5A, and 6). When the knife 420 is fully received within the knife cavity 808, the knife 420 may be characterized as being in a "fully retracted" or "home" position. Upon firing the end effector 204 (FIGS. 2 and 4A-4B), the drive rod 416 is moved (urged) distally, which correspondingly moves the knife 420 out of the knife cavity 808 and into the guide track 422 (FIG. 4A). After firing is complete, the drive rod 416 is retracted proximally, as shown by the arrow C, which pulls the knife 420 proximally and back into the knife cavity 808 until it is desired to fire the end effector 204 again.

In the illustrated embodiment, the knife cavity 808 is defined by the housing body 804, which provides opposing first (left) and second (right) walls 810*a* and 810*b* that extend from the distal end 806*a* of the knife housing 802 and toward the proximal end 806*b*. The knife cavity 808 encompasses a gap defined between the first and second walls 810*a,b*. In the illustrated embodiment, the walls 810*a,b* define corresponding control surfaces 812*a* and 812*b* configured to engage and reorient the knife 420 (FIGS. 4B, 5A, and 6) into alignment with the knife cavity 808. In the illustrated embodiment, each wall 810*a,b* provides a corresponding control surface 812*a,b*. In other embodiments, however, only one control surface 812*a,b* may be required to properly reorient the knife 420 into alignment with the knife cavity 808.

In the illustrated embodiment, each control surface 812*a,b* comprises an arcuate and ramped surface defined on the interior of the corresponding wall 810*a*. Moreover, the control surfaces 812*a,b* are oppositely angled to help reorient the knife 420 (FIGS. 4B, 5A, and 6) to its home position. More specifically, each control surface 812*a,b* extends from the distal end 806*a* of the knife housing 802 in a ramped and curved fashion toward the proximal end 806*b*. The control surfaces 812*a,b*, however, exhibit inverse orientations, which helps promote rotation of the knife 420 to align the knife 420 with the knife cavity 808. In some embodiments, the control surfaces 812*a,b* span the axial length of the walls 810*a,b*, respectively.

Figure 9A:
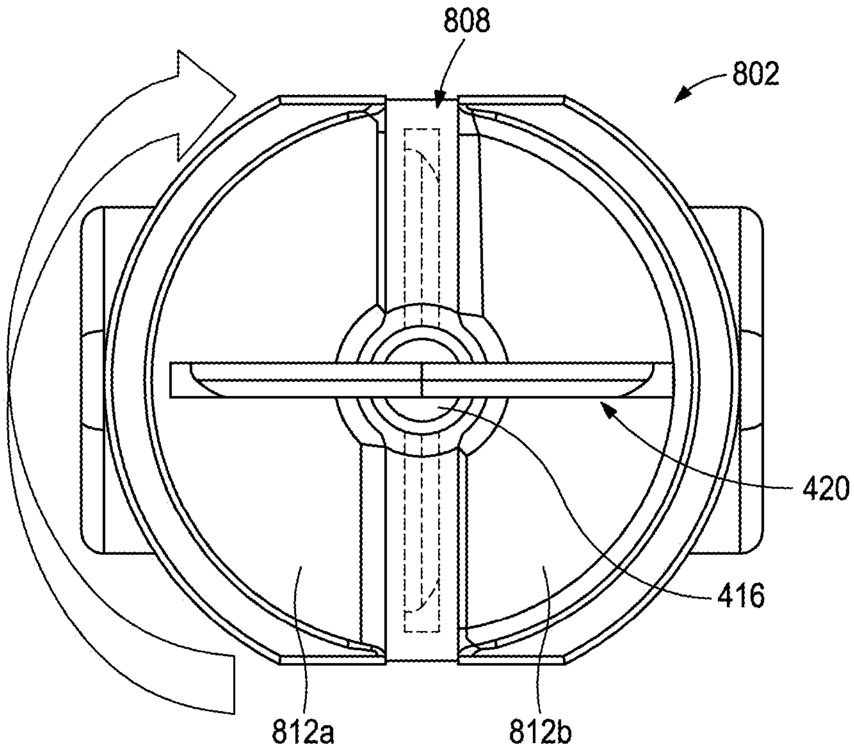
FIG. 9A is a front, end view of the knife housing of FIG. 8 showing example operation of reorienting the knife.
Figure 9B:
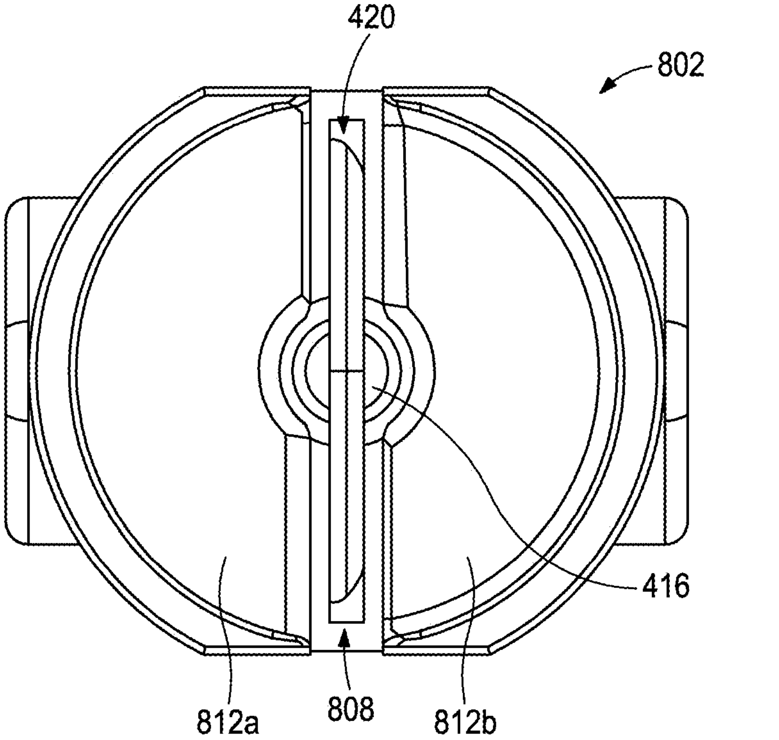
FIG. 9B is a front, end view of the knife housing of FIG. 8 showing a reoriented knife in its home position.

FIGS. 9A and 9B are end views of knife housing 802 showing example operation of reorienting the knife 420, according to one or more embodiments. As the drive rod 416 is moved proximally, the proximal end 514*b* (FIGS. 5A, 6) of the knife 420 will eventually locate and engage the control surfaces 812*a,b*, which help guide the knife 420 axially into the knife cavity 808. More specifically, the control surfaces 812*a,b* help the knife 420 rotate into alignment with knife cavity 808 as the knife 420 moves proximally.

In the illustrated example, the knife 420 is shown oriented generally horizontal as it approaches the knife housing 802 moving proximally. In this orientation, the knife 420 will be unable to reach its home position in knife cavity 808, which requires a generally vertical orientation. Upon reaching the knife housing 802, the proximal end 514*b* (FIGS. 5A, 6) of the knife 420 engages the control surfaces 812*a,b*, which cause the knife 420 to rotate into alignment with the knife cavity 808 as the knife 420 slidably engages the corresponding control surfaces 812*a,b*. Because the control surfaces 812*a,b* are oppositely angled, the knife 420 is induced into rotation to align with the knife cavity 808, and once properly aligned, further proximal movement of the drive rod 416 will correspondingly cause the knife 420 to reach its home position, as shown in FIG. 9B.

Figure 10A:
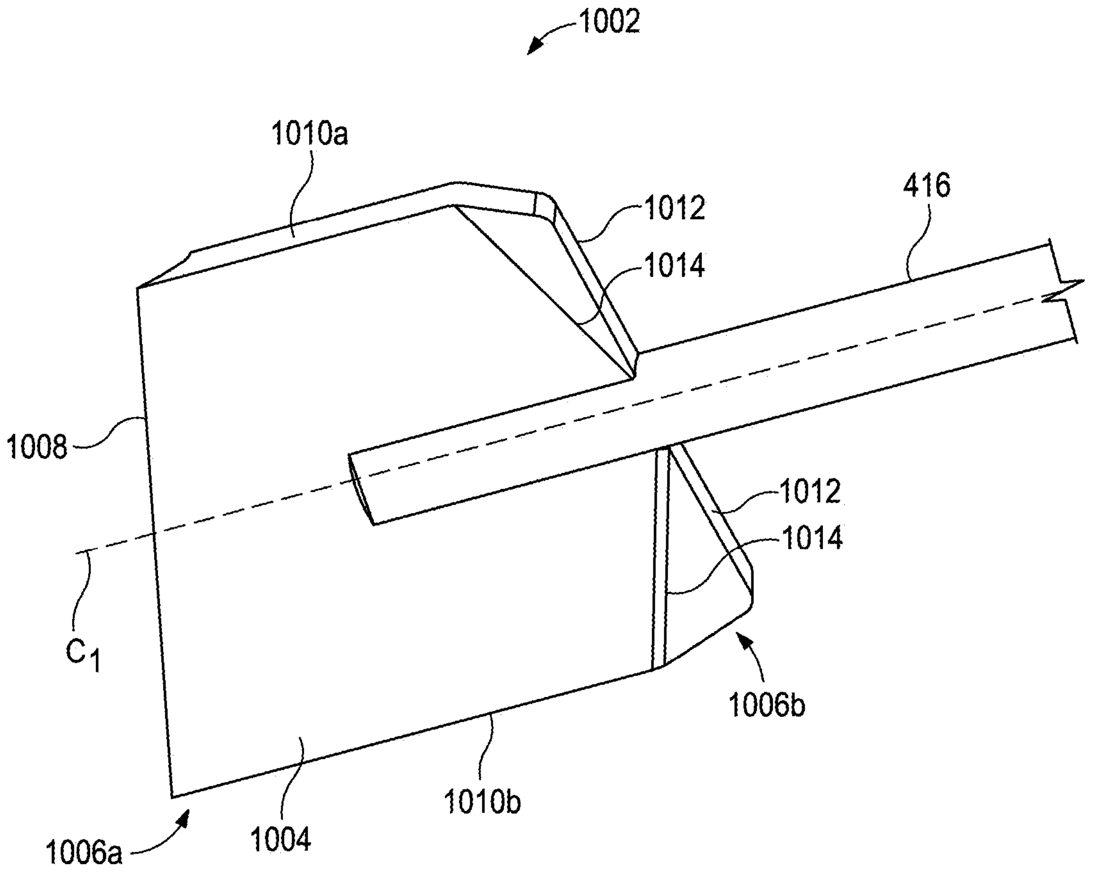
FIG. 10A is an isometric view of an example knife, according to one or more embodiments.

FIG. 10A is an isometric view of an example knife 1002, according to one or more additional embodiments of the present disclosure. The knife 1002 may be similar in some respects to the knife 420 of FIGS. 4B, 5A, 6, and 9A-9B, and therefore may be best understood with reference thereto. As illustrated, the knife 1002 includes a knife body 1004 having a first or "distal" end 1006*a* and a second or "proximal" end 1006*b* opposite the distal end 1006*a*. In some embodiments, the knife 1002 may be fabricated stainless-steel (e.g., 420 or 440 stainless steel). A cutting edge 1008 is provided and otherwise formed at the distal end 1006*a*. In some embodiments, as illustrated, the cutting edge 1008 may be straight and angled relative to a centerline $C_1$ of the knife 1002. The cutting edge 1008 may be angled, for example between about 5° and about 175° from the centerline $C_1$. In other embodiments, however, the cutting edge 1008 may be V-shaped, arcuate, or may exhibit any other geometry suitable to achieve desirable cutting properties.

The knife body 1004 may further include a first or "top" edge 1010*a* and a second or "bottom" edge 1010*b* opposite the top edge 1010*a*. The top and bottom edges 1010*a,b* extend between the distal and proximal ends 1006*a,b* of the body 1004.

As shown, the knife 1002 may be operatively coupled to the distal end of drive rod 416, and longitudinal movement (translation) of the drive rod 416 correspondingly moves the knife 1002 within the guide track(s) 422 (FIG. 4B) to sever tissue with the cutting edge 1008.

In some embodiments, as illustrated, one or more modified edge features or "flutes" 1012 may be provided at the proximal end 1006*b* of the knife 1002. In the illustrated embodiment, the knife 1002 has a first or "top" flute 1012 extending between the drive rod 416 and the top edge 1010*a*, and a bottom flute 1012 extending between the drive rod 416 and the bottom edge 1010*b*.

In at least one embodiment, the flutes 1012 may be formed by bending corresponding portions of the proximal end 1006*b* such that the flutes 1012 extend in a plane that is not parallel with a plane extending through the body 1004. The flutes 1012 may be formed for example, by bending the body 1004 along precision score lines 1014 created with photochemical machining (PCM). Advantages of using PCM include burr-free and stress-free machining. As illustrated, the top and bottom flutes 1012 may be bent in opposing directions; i.e., toward opposing sides of the body 1004.

Figure 10B:
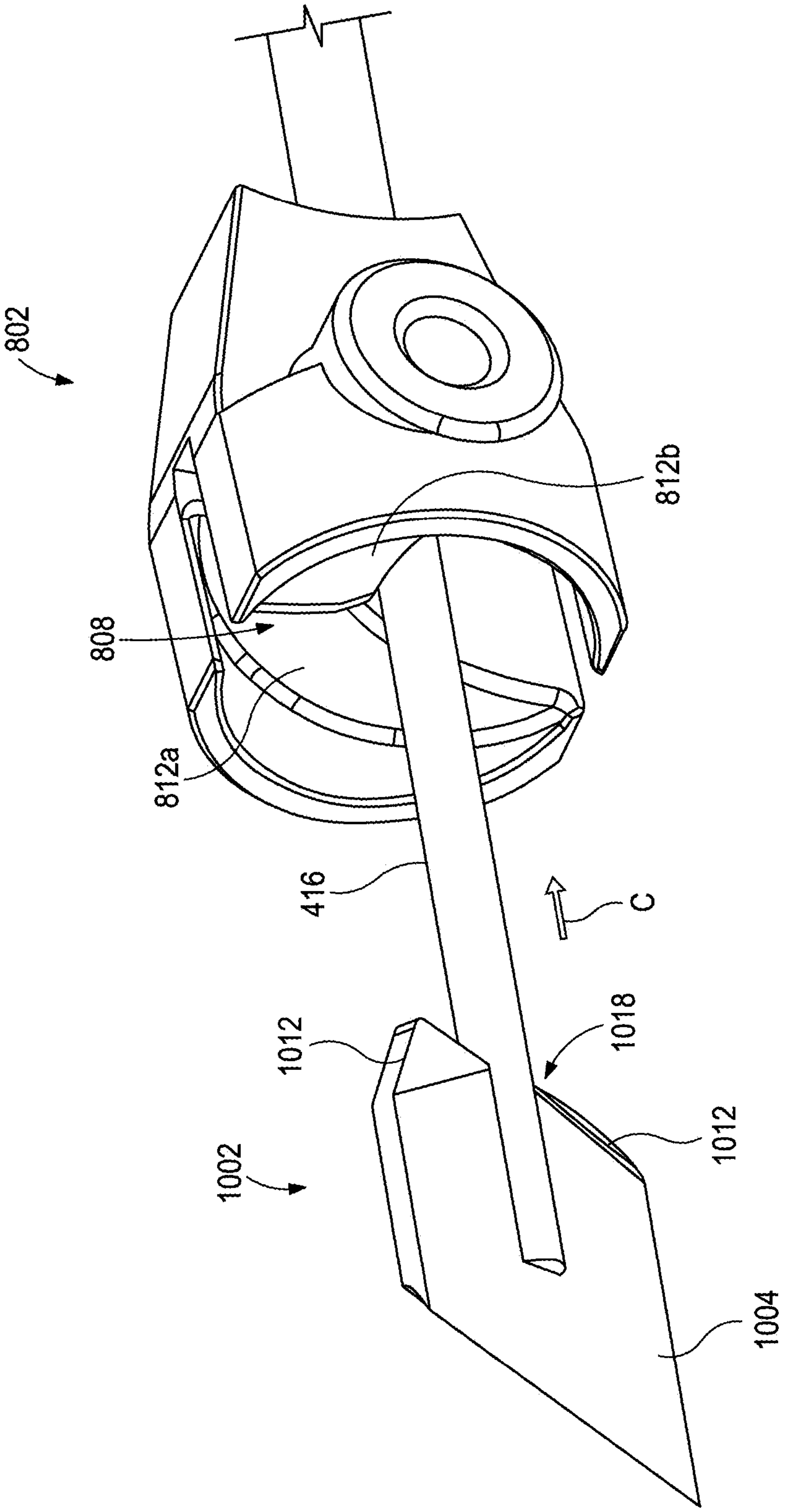
FIG. 10B is an isometric view of the knife of FIG. 10A showing example contact of the knife with the knife housing of FIG. 8, according to one or more embodiments.

FIG. 10B is an isometric view of the knife 1002 and the knife housing 802 showing example homing of the knife 1002 in the knife cavity 808, according to one or more embodiments. As the drive rod 416 moves proximally C, the knife 1002 will correspondingly move in the same direction. If the knife 1002 is not properly aligned with the knife cavity 808, the flutes 1012 will eventually come into contact with the control surfaces 812*a,b*. More specifically, the bottom flute 1012 may engage the first control surface 812*a*, while the top flute 1012 may engage the second control surface 812*b*. Further proximal C movement of the knife 1002 will cause the flutes 1012 to slidingly engage the control surfaces 812*a,b*, which causes the knife 420 to rotate into alignment with the knife cavity 808. Because the control surfaces 812*a,b* are oppositely angled (e.g., inverse orientation), the knife 1002 is induced into rotation to align with the knife cavity 808. Once aligned with the knife cavity 808, further proximal C movement of the drive rod 416 will correspondingly cause the knife 1002 to enter the knife cavity 808 and ultimately reach its home position.

The angled geometry of the flutes 1012 helps to enhance the rotational effect caused by the control surfaces 812*a,b*. In some embodiments, the flutes 1012 may be angled from the body 1004 between about 5° and about 85° relative to a plane extending through the body 1004.

While top and bottom flutes 1012 are shown in FIGS. 10A-10B, it is contemplated herein to have only one flute 1012. In such embodiments, the knife housing 802 could have one or two control surfaces 812*a,b*, but preferably two control surfaces 812*a,b*. In other embodiments, the knife housing 802 may omit control surfaces 812*a,b*, and the knife 1002 may have two (top and bottom) flutes 1012. In such embodiments, the flutes 1012 may act as control surfaces to induce rotation of the knife 1002 as engaging the knife housing 802 to return to the home position without an angled control surface.

In some embodiments, control surfaces may be provided, but not on the knife housing 802. More specifically, it is contemplated herein to provide angled or arcuate control surfaces on the electrode(s) 414 (FIG. 4A), within the guide track(s) 422 (FIG. 4B), or as a feature located distal to the knife housing 802. In such embodiments, the control surface(s) may be configured to urge the knife into rotation and thereby angularly align with the knife cavity 808.

Embodiments disclosed herein include:

A. A surgical tool includes a drive housing, a shaft extending distally from the drive housing, and an end effector arranged at an end of the shaft and including a knife housing having opposing distal and proximal ends and opposing left and right walls extending from the distal end toward the proximal end, the left and right walls defining a knife cavity therebetween, a control surface defined on at least one of the left and right walls, and a knife having opposing distal and proximal ends and being moveable distally out of the knife cavity and proximally to a fully retracted position within the knife cavity, wherein, when the knife is moved proximally toward the fully retracted position, the proximal end of the knife is engageable with the control surface, which causes the knife to rotate into alignment with the knife cavity.

B. An end effector for a surgical tool includes a knife housing having opposing distal and proximal ends and opposing left and right walls extending from the distal end toward the proximal end, the left and right walls defining a knife cavity therebetween, a control surface defined on at least one of the left and right walls, and a knife having opposing distal and proximal ends and being moveable distally out of the knife cavity and proximally to a fully retracted position within the knife cavity, wherein, when the knife is moved proximally toward the fully retracted position, the proximal end of the knife is engageable with the control surface, which causes the knife to rotate into alignment with the knife cavity.

C. A method of using an end effector includes advancing a knife distally and out of a knife housing, the knife housing including opposing distal and proximal ends and opposing left and right walls extending from the distal end toward the proximal end, the left and right walls defining a knife cavity therebetween, and a control surface defined on at least one of the left and right walls, retracting the knife proximally toward the knife housing and engaging a proximal end of the knife on the control surface; causing the knife to rotate into alignment with the knife cavity as the knife moves proximally and slidably engages the control surface, and receiving the knife in a fully retracted position within the knife cavity.

Each of embodiments A, B, and C may have one or more of the following additional elements in any combination: Element 1: wherein the left and right walls extend substantially parallel to each other. Element 2: wherein the proximal end of the knife slidably engages the control surface. Element 3: wherein the control surface comprises a first control surface defined on the left wall and the end effector further includes a second control surface defined on the right wall. Element 4: wherein the first and second control surfaces each comprise a straight and angled surface, and wherein the angled surface of the first control surface is oppositely angled from the angled surface of the second control surface. Element 5: wherein the first and second control surfaces each comprise a ramped and arcuate surface, and wherein the arcuate surface of the first control surface is inverse from the arcuate surface of the second control surface. Element 6: wherein the first and second control surfaces each span the axial length of the left and right walls, respectively. Element 7: wherein the end effector includes opposing upper and lower jaws actuatable between open and closed positions, and wherein, when the jaws are in the open position, a plane extending along an exposed surface of the upper jaw intersects the control surface. Element 8: further comprising a drive rod extending from the drive housing and within the shaft, the drive rod being operatively coupled to the proximal end of the knife such that longitudinal movement of the drive rod correspondingly moves the knife relative to the knife housing. Element 9: further comprising a rod sheath operatively coupled to the proximal end of the knife housing, wherein the drive rod translates within the rod sheath. Element 10: wherein the knife includes a body having top edge and a bottom edge, each edge extending between the distal and proximal ends of the knife, a flute provided at the proximal end and extending from one of the top or bottom edge toward the drive rod, wherein the flute extends in a plane that is not parallel with a plane extending through the body. Element 11: wherein the flute comprises a first flute extending from the top edge toward the drive rod, and wherein the proximal end of the knife further comprises a second flute extending from the bottom edge toward the drive rod.

Element 12: wherein the proximal end of the knife slidably engages the control surface. Element 13: wherein the control surface comprises a first control surface defined on the left wall and a second control surface defined on the right wall. Element 14: wherein the first and second control surfaces each comprise a straight and angled surface, and wherein the angled surface of the first control surface is oppositely angled from the angled surface of the second control surface. Element 15: wherein the first and second control surfaces each comprise a ramped and arcuate surface, and wherein the arcuate surface of the first control surface is inverse from the arcuate surface of the second control surface. Element 16: wherein the first and second control surfaces each span the axial length of the left and right walls, respectively. Element 17: wherein the end effector includes opposing upper and lower jaws actuatable between open and closed positions, and wherein, when the jaws are in the open position, a plane extending along an exposed surface of the upper jaw intersects the control surface.

By way of non-limiting example, exemplary combinations applicable to A, B, and C include: Element 3 with Element 4; Element 3 with Element 5; Element 5 with Element 6; Element 9 with Element 10; Element 10 with Element 11; Element 13 with Element 14; Element 13 with Element 15; and Element 15 with Element 16.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A surgical tool, comprising:
- a drive housing;
- a shaft extending distally from the drive housing; and
- an end effector arranged at an end of the shaft and including:
  - a knife housing having opposing distal and proximal ends and opposing left and right walls extending from the distal end toward the proximal end, the left and right walls defining a knife cavity therebetween;
  - a control surface defined on at least one of the left and right walls; and
  - a knife having opposing distal and proximal ends and being moveable distally out of the knife cavity and proximally to a fully retracted position within the knife cavity,
- wherein, when the knife is moved proximally toward the fully retracted position, the proximal end of the knife is engageable with the control surface, which causes the knife to rotate into alignment with the knife cavity.

2. The surgical tool of claim 1, wherein the left and right walls extend parallel to each other.

3. The surgical tool of claim 1, wherein the proximal end of the knife slidably engages the control surface.

4. The surgical tool of claim 1, wherein the control surface comprises a first control surface defined on the left wall and the end effector further includes a second control surface defined on the right wall.

5. The surgical tool of claim 4, wherein the first and second control surfaces each comprise a straight and angled surface, and wherein the angled surface of the first control surface is oppositely angled from the angled surface of the second control surface.

6. The surgical tool of claim 4, wherein the first and second control surfaces each comprise a ramped and arcuate surface, and wherein the arcuate surface of the first control surface is inverse from the arcuate surface of the second control surface.

7. The surgical tool of claim 6, wherein the first and second control surfaces each span the axial length of the left and right walls, respectively.

8. The surgical tool of claim 1, wherein the end effector includes opposing upper and lower jaws actuatable between open and closed positions, and wherein, when the jaws are in the open position, a plane extending along an exposed surface of the upper jaw intersects the control surface.

9. The surgical tool of claim 1, further comprising a drive rod extending from the drive housing and within the shaft, the drive rod being operatively coupled to the proximal end of the knife such that longitudinal movement of the drive rod correspondingly moves the knife relative to the knife housing.

10. The surgical tool of claim 9, further comprising a rod sheath operatively coupled to the proximal end of the knife housing, wherein the drive rod translates within the rod sheath.

11. The surgical tool of claim 9, wherein the knife includes:
- a body having top edge and a bottom edge, each edge extending between the distal and proximal ends of the knife; and
- a flute provided at the proximal end and extending from one of the top or bottom edge toward the drive rod,
- wherein the flute extends in a plane that is not parallel with a plane extending through the body.

12. The surgical tool of claim 11, wherein the flute comprises a first flute extending from the top edge toward the drive rod, and wherein the proximal end of the knife further comprises a second flute extending from the bottom edge toward the drive rod.

13. An end effector for a surgical tool, comprising:
- a knife housing having opposing distal and proximal ends and opposing left and right walls extending from the distal end toward the proximal end, the left and right walls defining a knife cavity therebetween;
- a control surface defined on at least one of the left and right walls; and
- a knife having opposing distal and proximal ends and being moveable distally out of the knife cavity and proximally to a fully retracted position within the knife cavity,
- wherein, when the knife is moved proximally toward the fully retracted position, the proximal end of the knife is engageable with the control surface, which causes the knife to rotate into alignment with the knife cavity.

14. The end effector of claim 13, wherein the proximal end of the knife slidably engages the control surface.

15. The end effector of claim 13, wherein the control surface comprises a first control surface defined on the left wall and a second control surface defined on the right wall.

16. The end effector of claim 15, wherein the first and second control surfaces each comprise a straight and angled surface, and wherein the angled surface of the first control surface is oppositely angled from the angled surface of the second control surface.

17. The end effector of claim 15, wherein the first and second control surfaces each comprise a ramped and arcuate surface, and wherein the arcuate surface of the first control surface is inverse from the arcuate surface of the second control surface.

18. The end effector of claim 17, wherein the first and second control surfaces each span the axial length of the left and right walls, respectively.

19. The end effector of claim 13, wherein the end effector includes opposing upper and lower jaws actuatable between open and closed positions, and wherein, when the jaws are in the open position, a plane extending along an exposed surface of the upper jaw intersects the control surface.

20. A method of using an end effector, comprising:
advancing a knife distally and out of a knife housing, the knife housing including:
opposing distal and proximal ends and opposing left and right walls extending from the distal end toward the proximal end, the left and right walls defining a knife cavity therebetween; and
a control surface defined on at least one of the left and right walls;
retracting the knife proximally toward the knife housing and engaging a proximal end of the knife on the control surface;
causing the knife to rotate into alignment with the knife cavity as the knife moves proximally and slidably engages the control surface; and
receiving the knife in a fully retracted position within the knife cavity.

* * * * *